United States Patent [19]

Crankshaw et al.

[11] Patent Number: 4,741,732
[45] Date of Patent: May 3, 1988

[54] OPEN-LOOP CONTROL OF DRUG INFUSION

[75] Inventors: David P. Crankshaw, Toorak; Malcolm D. Boyd, Kew, both of Australia

[73] Assignee: The University of Melbourne, Victoria, Australia

[21] Appl. No.: 732,147

[22] Filed: May 9, 1985

[30] Foreign Application Priority Data

May 10, 1984 [AU] Australia .............................. PG4934

[51] Int. Cl.⁴ .............................................. A61M 5/00
[52] U.S. Cl. ....................................... 604/50; 604/67; 604/65; 604/155
[58] Field of Search ...................... 604/67, 65, 50, 154, 604/155

[56] References Cited

U.S. PATENT DOCUMENTS 3,701,345 10/1962 Heilman et al. ...................... 604/67
4,320,757 3/1982 Whitney et al. ...................... 604/67

Primary Examiner—Albert W. Davis, Jr.
Attorney, Agent, or Firm—Bernard, Rothwell & Brown

[57] ABSTRACT

A method of determining a generalised infusion rate profile for the delivery of drugs into the circulation comprising the steps of:

(a) infusing a drug at arbitrary but known rates into a group of patients for each of whom the Lean Body Mass has been determined;

(b) determining the plasma arterial concentration of the drug in each patient at a number of specific time intervals throughout each infusion period;

(c) for each patient, estimating the rates of loss of drug from the circulation at a number of specific time instants by dividing the known infusion rates per Lean Body Mass of these instants by the plasma arterial concentrations of the drug at each of these instants;

(d) calculating the average of the estimated rates of loss of drug from the circulation per Lean Body Mass unit at each specific time interval for the group of patients;

(e) interpolating the successive average points between the specific time intervals to produce an infusion profile;

(f) infusing said drug in accordance with said infusion profile determined from said interpolations into a group of patients for each of whom the Lean Body Mass has been determined, said infusion rate being scaled according to said Lean Body Mass of each patient, and (g) repeating steps (b) to (f) until a desired steady plasma arterial content of the drug is substantially maintained throughout the infusion period.

29 Claims, 11 Drawing Sheets

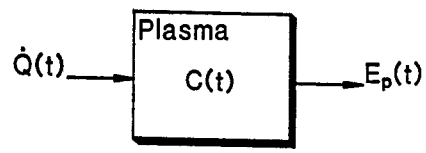
FIG_3.
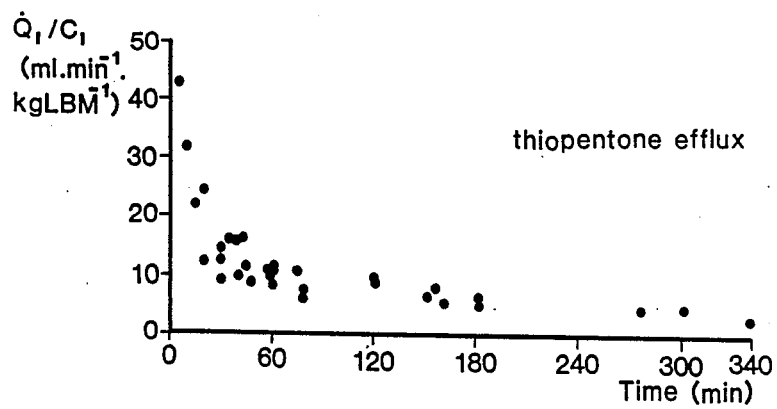
FIG_4.
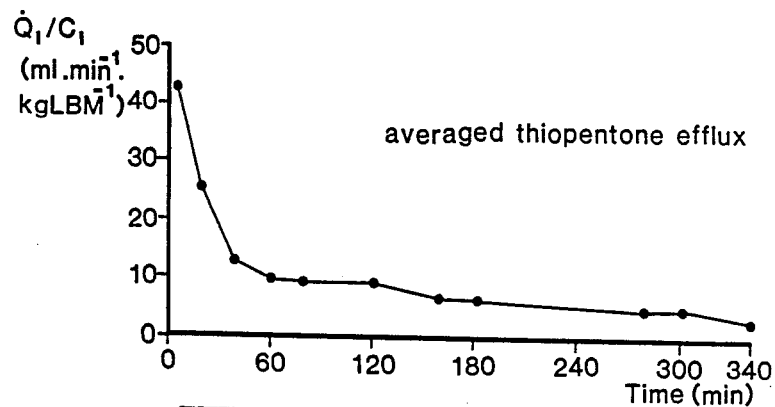
FIG_5.

OPEN-LOOP CONTROL OF DRUG INFUSION

FIELD OF THE INVENTION

The present invention is directed to a method, to techniques for applying the method and to apparatus which will permit the rapid attainment and the maintenance of a substantially constant concentration in the arterial blood plasma of an intravenously administered drug. In one preferred form, the method and apparatus are applied to the intravenous administration of drugs which produce sedation, anaesthesia, analgesia or muscle paralysis, in association with anaesthetic practice.

BACKGROUND OF THE INVENTION

At the present time there is a major problem in establishing and maintaining a constant concentration of drugs that are administered intravenously to maintain anaesthesia. It is known in general terms that to achieve a constant concentration of a drug in the arterial blood plasma it is necessary to administer a bolus dose of the drug to establish an initial level, followed by an infusion of the drug to maintain the level over a period of time. Methods used to date to implement this general idea are based on conventional pharmacokinetic analysis where predictions are made from studies based on the administration of single doses of a drug.

To use such methods it is first necessary to mathematically describe the loss from the body of a single dose of the particular drug. The single dose of the drug is administered to a subject and then samples of blood are drawn over a number of days in order to define the decay in the concentration of the drug in the blood plasma. Then, using the mathematical process of residuals or by nonlinear least-square regression analysis, one or more pairs of exponential coefficients are derived to describe the decay of the curve to the zero point at infinite time (see FIG. 1). A description of this method is provided in detail by Gibaldi, M. and Perrier, D., "Pharmacokinetics" Marcel Dekker Inc., New York, 1982, pp 433 and 475)

Also, from the elimination profile the clearance (Cl) of the drug by metabolism or excretion from the body may be obtained by:

$$Cl = dose/AUC$$

where the plasma concentration/time curve is integrated (AUC) for up to three days following the administration of the dose of the drug, again see Gibaldi and Perrier, p. 321.

Once the coefficients of the decay curve and the clearance of the drug have been determined, it then becomes possible using mathematical transforms to create a mathematical model which simulates the distribution and elimination of the *single* dose of the drug. The model consists of compartments described in terms of their volume (eg. V1, V2 and V3) and rate constants (eg. k12, k21, k13, k31 and k10) for the movement of drug to and fro between the compartments (see (FIG. 2). The loss of drug from the system by detoxification or excretion is described either by an elimination rate constant or by the clearance of the drug from the particular patient. Such methods are fully described in many tests, particularly by Gibaldi and Perrier at pp 45–111.

Once such a mathematical model of the subject has been created it then becomes possible to design infusion patterns in an attempt to achieve a steady concentration.

Earliest methods of infusion have involved the injection of a single dose of the drug followed by a constant rate infusion. The infusion is used to counteract loss of drug by elimination while the single dose, based on the amount of drug required either, to reach the desired concentration in the initial volume of distribution (V1 in FIG. 2) or in the steady state volume of distribution (V1 +V2+V3 in FIG. 2), is used to establish an initial concentration. Both these methods however ignore the time related movement of drug between the compartments and have proved unsatisfactory for many drugs, particularly anaesthetic drugs which are lost rapidly from the circulation. The situation is compounded further for many anaesthetic drugs as they have very narrow ranges of safety making it highly desirably to hold concentrations close to that desired by the operator.

Various approaches have been described in an attempt to overcome the problem of rapid loss of drug to the tissues and the consequent, highly undesirable, fluctuations in blood concentration. Some involve either substitution of a short term loading infusion for the initial bolus or alternatively the addition of a smaller loading infusion to the bolus and maintenance doses.

The most popular methods of infusion, however, utilize the coefficients of the compartmental model (FIG. 2) derived using the methods outlined above and averaged for a number of patients to derive exponential infusions. The parameters of the model are used as a basis for calculating an infusion profile which will keep the concentration constant in the central compartment of the model on the assumption that the patient will behave as the model. Such a method results in a mono- or polyexponentially decaying infusion profile asymptoting to a constant rate which relates to the anticipated constant rate of elimination of the drug at a steady plasma concentration. The constant rate (assymptote) varies considerably between drugs, being determined by the ability of the patient to detoxify or excrete the drug. Such methods combining bolus, exponential decaying infusion and maintenance rate infusion have been described in theory by Kruger-Thiemer, E. in "Continuous intravenous infusion and multicompartment accumulation" in European Journal of Pharmacology, pp 317–324, Volume 4, (1968) and by Vaughan, D. P. and Tucker, G. T. in "General derivation of the ideal intravenous drug input required to achieve and maintain a constant plasma drug concentration. Theoretical application to lignocaine therapy." in European Journal of Clinical Pharmacology, pp 433–440, Volume 10, 1976.

A practical use of the exponential method, in particular the use of a computer to perform the required transforms and control the rate of a drug delivery device, has been described by Schwilden H., Schuttler J., Stoeckel H. G. and Lauven P. M. in "Strategies of Infusion for Intravenous Anaesthesia" in Pharmacological Basis of Anesthesiology, eds Tiengo M. and Cousins M. J., Raven Press, 1983. These authors describe a method where it is necessary to store in the memory of a computer averaged kinetic data, ie. the compartmental parameters shown in FIG. 2, for each drug as well as appropriate programs to perform the considerable mathematical operations required. Then, prior to an infusion, the operator nominates the concentration required in the plasma of the subject. Then by a method, of the type described by Kruger-Theimer, an infusion pattern is computed as time passes, the magnitude of which is used to control the rate of a drug delivery device.

Various other approaches to the generation of exponential infusions have been described which use pneumatic or electrical means. One such method is described by Stoffregen (German Patent Application DE No. 3227518 A1 - 24 July, 1981) which produces a mono-exponential decay. This method while apparently novel in electronic technique uses the well known exponential method and further does not appear to offer any means of generating a polyexponential decay. Also the method does not describe any means of adapting the infusion rate to achieve a nominated arterial plasma concentration of the drug or to vary the base rate of infusion in accordance with rate of elimination of the particular drug in use.

SUMMARY OF THE INVENTION

The present invention recognizes:

(i) that conditions following a single dose, by comparison with those during an infusion may well be different, particularly for drugs that have a significant effect on the rate of flow of blood through the heart and to the various organs of the body.

(ii) that conditions of drug distribution and elimination are unlikely to be the same during an infusion at therapeutic levels as they are during the hours and days following a single dose, (iii) that therapeutic levels of a drug may affect the distribution of a drug to the various tissues, particularly those where detoxification occurs.

(iv) that single dose drug elimination curves may be quite inaccurate at the extreme ends so that the early part suffers because of extrapolation and the later part because of the extremely low drug levels involved which lead to errors in the assay.

(v) that time related changes in the circulation may occur resulting in corresponding changes with time of the parameters of the kinetic model.

(vi) that drugs which produce unconsciousness cause falling levels of adrenaline and other substances which in turn alter circulatory and metabolic function, and (vii) that for an infusion to be applicable to a wide variety of subjects and to be able to achieve a nominated level of the drug in a subject, some formal method is required to relate drug delivery to a measurable physical parameter which is widely applicable to subjects of varying age and morphology.

Central to the approach used in this method is the development of a new concept in pharmacokinetics, the Plasma Drug Efflux. This concept simply stated is that at any instant, if the plasma concentration of a drug is neither rising nor falling, the rate of delivery of the drug to the circulation ie. the infusion rate, must equate to the rate at which the drug is being lost form the circulation, it being unimportant whether the loss, is by distribution, metabolism or excretion.

If, by way of illustration, the blood plasma is represented as a single compartment of undetermined volume the infusion scheme may be represented as shown in FIG. 3. Then if drug is administered by some arbitrary infusion scheme Q(t), the plasma concentration is C(t) and the rate of drug loss from the plasma may be called the Plasma Drug Efflux, $E_p(t)$.

If the plasma drug concentration is constant so that the amount of drug is not changing then the instantaneous rate of drug influx to the plasma (the infusion rate), and the instantaneous concentration in the plasma may be used as an estimate of drug efflux from the plasma, as an estimate of i.e.:

$$E_p \approx Q_I/C_I$$

The efflux estimate may then be plotted against time, and will essentially describe a dosing-rate/concentration profile as a function of time which will result in a plateau concentration for all time.

In practice in applying this method it is not possible at first to achieve a constant plasma concentration as this is, of course, the goal of the method. But it is possible by the use of very few iterations to closely approach this goal.

Thus, according to the first aspects, the present invention provides a method of determining a generalised infusion rate profile for the delivery of drugs into the circulation comprising the steps of:

(a) infusing a drug at arbitrary but known rates into a group of patients for each of whom the Lean Body Mass has been determined;

(b) determining the plasma arterial concentration of the drug in each patient at a number of specific time intervals throughout each infusion period;

(c) for each patient, estimating the rates of loss of drug from the circulation at a number of specific time instants by dividing the known infusion rates per Lean Body Mass at these instants by the plasma arterial concentrations of the drug at each of these instants.

(d) calculating the average of the estimated rates of loss of drug from the circulation per Lean Body Mass unit at each specific time interval for the group of patients;

(e) interpolating the successive average points between the specific time intervals to produce an infusion profile;

(f) infusing said drug in accordance with said infusion profile determined from said interpolations into a group of patients for each of whom the Lean Body Mass has been determined, said infusion rate being scaled according to said Lean Body Mass of each patient, and (g) repeating steps (b) to (f) until a desired steady plasma arterial content of the drug is substantially maintained throughout the infusion period. It must be emphasized that the shape of each infusion profile, except for the first in the series, can be determined entirely by the results obtained from the previous infusion group and that no mathematical function is assigned or required by the method.

The invention also provides a method of infusion of a drug into a patient comprising the steps of:

(i) determining the Lean Body Mass of the patient:

(ii) selecting a predetermined profile for the rate of delivery of drug, which rate varies with time and is configured to maintain a selected substantially steady plasma arterial content of the drug in the patient throughout an infusion period;

(iii) scaling said predetermined profile by the determined Lean Body Mass of the patient and by the desired substantially level arterial plasma concentration of drug to be maintained in the system of the patient, and (iv) administering the drug to the patient in accordance with said scaled profile by means of an infusion device which is controlled to deliver said drug at said scaled infusion rate profile.

Still further the invention provides a system for achieving the method of infusion comprising an infusion system for regulating the delivery of a drug to a patient, including control means for controlling the operation of an infusion pump, said control means including pre-programmed means for varying the invusion rate with respect to elapsed time, said pre-programmed means varying the infusion rate in accordance with a profile which varies with time and which is adapted to maintain a desired substantially steady plasma arterial content of the drug throughout the infusion period, and operator adjustable scaling means for setting the desired concentration of said drug in the patient and for setting the Lean Body Mass of the patient, said scaling means causing modification of the pre-programmed infusion rate by a fixed proportion over each time period of operation of said infusion pump.

The invention also provides an infusion apparatus by means of which the method and system may be realized, comprising an infusion pump comprising means for receiving a syringe containing a fluid to be administered, syringe actuator means and means for driving said actuator means to move the plunger of said syringe to deliver fluid therefrom, characterised in that said drive means includes a permanently maintained connection between said drive means and a position sensing device by means of which the position of said actuator means is monitored at all times.

BRIEF DESCRIPTION OF THE DRAWINGS

A preferred embodiment of each aspect of the invention will now be described with reference to the accompanying drawings in which:

FIG. 3 is a diagram illustrating one model explaining the basis of the method of the present invention;

FIG. 4 is a graph showing the Plasma Drug Efflux data of a first group of patients to the drug thiopentone (thiopental);

FIG. 4 is a graph showing the average of the data point in FIG. 4 interpolated to produce an Efflux profile;

DESCRIPTION OF PREFERRED EMBODIMENTS

Describing first the preferred method of defining a generalised infusion rate profile as applied to anaesthetic drugs, the method comprises the steps of:

(a) first determining the lean body mass (LBM) of a group of subjects. A convenient way of doing this in human subjects is to use the method described by Hallynck T.H. et al in "Should clearance be normalized to body surface of to lean body mass?" in British Journal of Clinical Pharmacology, pp 523–526, Volume 11, (1981), who presented the following formulae:

Males:
$LBM = 1.10 \times weight - 128 \times (weight^2/height^2)$

Females: $LBM = 1.07 \times weight - 148 \times (weight^2/height^2)$ (b) Following administration of a suitable bolus dose of a desired drug to achieve unconsciousness, the drug is infused at an arbitrary but known rate throughout the infusion. This arbitrary infusion can be a constant rate infusion, a stepped rate infusion, an infusion pattern derived using the compartmental (Kruger-Thiemer) technique described above or an infusion pattern derived by the present method for a different drug which is known to have similar properties to the drug under test.

(c) From this inital set of results and by knowing the rate of infusion throughout, whatever the pattern, as well as the sex, height and weight of each patient a set of data points can be obtained relating the infusion rate to the plasma arterial concentration at various times (FIG. 4).

(d) By averaging the amplitude of the data points within specific time periods and interpolating the resulting points (FIG. 5) an estimate of the Plasma Drug Efflux profile is thus obtained.

This estimate of the Efflux, expressed in terms of millilitres of blood cleared of drug per minute per kilogram lean body mass thus becomes the prescription for the infusion profile for the next group of subjects.

(e) Then by using the same method of dosing but now applying the dosage in terms of the estimated Efflux of the drug and the LBM, plasma concentrations will approach a constant and desired level without any intervention on the part of the operator.

(f) Iterations of this method may then be repeated three of four times if further precision is needed.

This is thus a new infusion profile which completely bypasses the conventional, single dose derived compartmental model described earlier in this specification. In doing this, a definition of the error for infusion dosing based on the conventional approach is also achieved. The rate profile is now derived under actual infusion dosing conditions, and is clearly a more valid approximation to the ideal infusion function.

Figure 1:
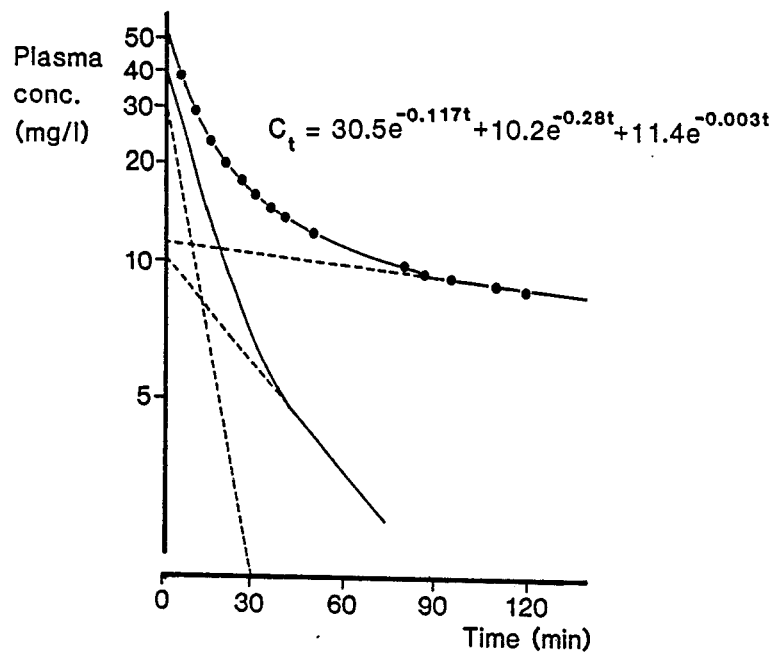
FIG. 1 is a graph showing the basis of prior art methods of infusion.
Figure 2:
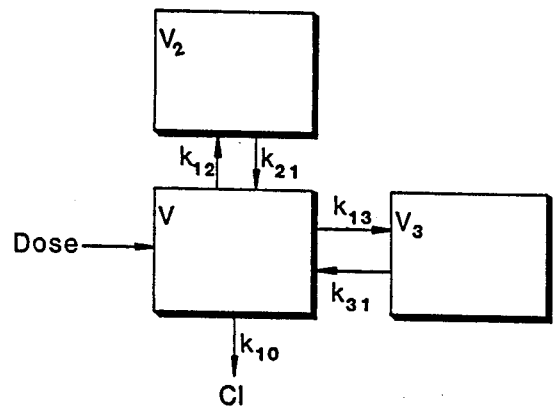
FIG. 2 is a diagram showing the basis of the compartmental model of drug distribution and elimination.
Figure 6:
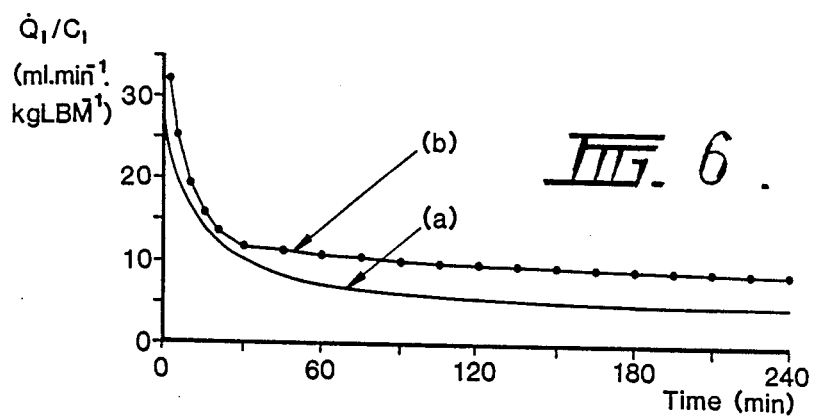
FIG. 6 is a graph showing the Efflux profile (b) after two iterations and the profile (a) based on the Kruger-Thiemer method.

FIG. 6 presents a comparison between the curve of anaesthetic agent thiopentone (thiopental) for a conventional infusion rate function, based on the method of Kruger-Thiemer labelled (a), with the derived Plasma Efflux profile after two iterations normalized for plasma level, and based on actual infusion data, labelled (b).

A comparison of the curves shown in FIG. 6 reveals:

(i) the rate of the new profile is much higher than the previous curve as time progresses,
(ii) the new profile is 10 to 20% higher in the early phases than the previous curve,
(iii) the new profile is around 50-100% higher than the old curve from about 30 minutes onwards.

The initial high level of the new profile indicates that a much higher initial infusion rate is required, quickly forcing the plasma concentration to the required level, then a rate which is about twice the conventional rate, thus holding the plasma concentration at the desired level and indicating the marked difference in the circulation during this period from that predicted by the Kruger-Theimer method.

It must be appreciated that an infusion rate that is half that actually required to achieve the desired level will result in approximately half the arterial plasma concentration during that period of the infusion.

Figure 10:
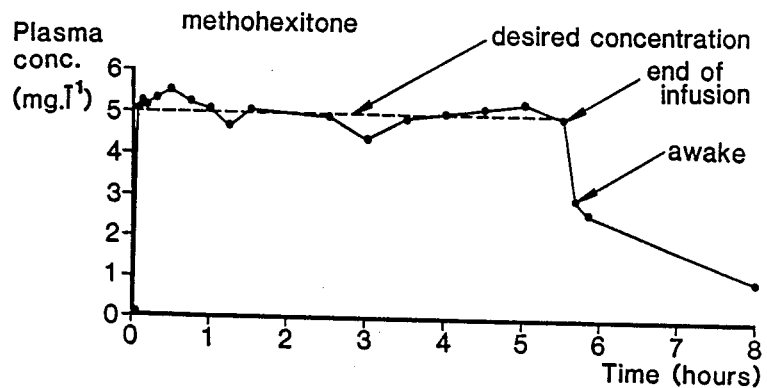
FIG. 10 is a graph of the arterial plasma concentration of methohexitone in a patient showing a substantially constant level at the desired concentration for the whole period.
Figure 11:
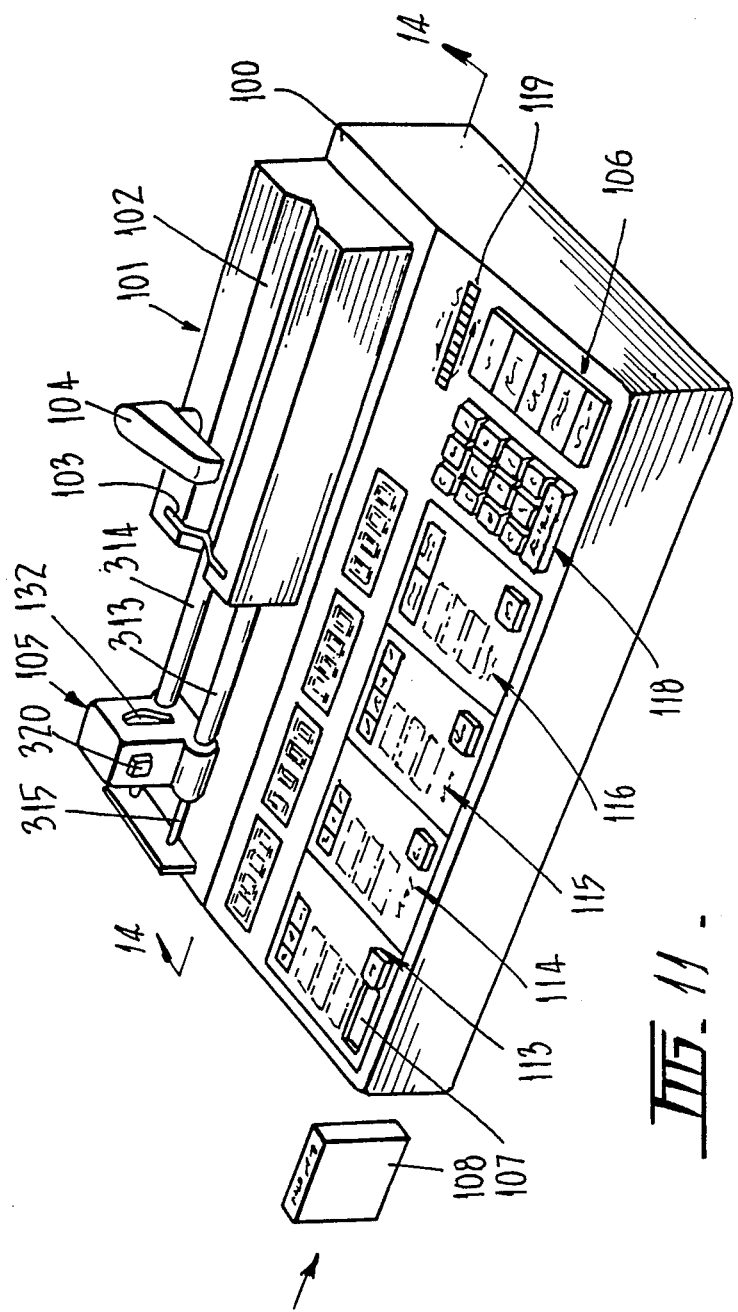
FIG. 11 is a perspective view of a preferred infusion pump.

As stated above, some drugs, particularly those used in anaesthesia, must be used within a narrow range of concentrations. If, for example, the concentration of methohexitone (FIG. 10) moves from a normally desired level of 4 to 6 mg/l to 10 mg/l the severe depression of the heart and breathing may occur while a fall to below 3 mg/l is likely to result in wakening of the patient.

As described above the plasma drug efflux profile presented in FIG. 6 is normalized to unit plasma concentration and unit patient lean body mass.

In order to apply the data presented in FIG. 6 to a practical infusion device, it is necessary to multiply the amplitude of the plasma drug efflux curve first by a numerical value representing the size of the patient (Lean Body Mass), and secondly, by a numerical value representing the actual plasma concentration of the drug required by the operator.

Figure 7:
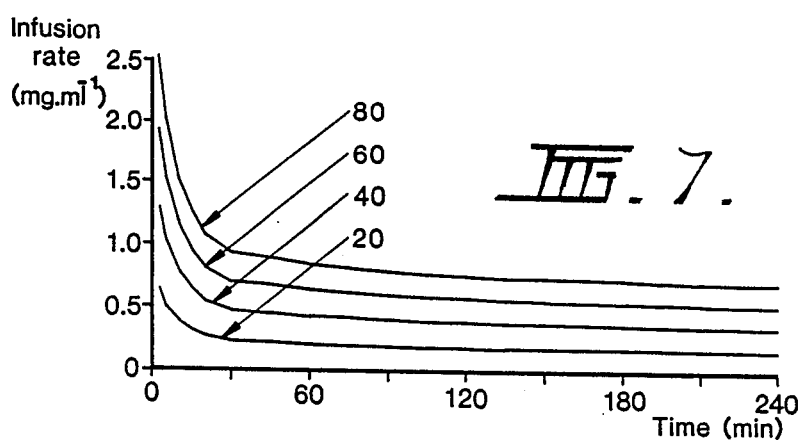
FIGS. 7 and 8 are graphs showing the infusion rates required for patients of indicated Lean Body Mass (LBM) and for different desired plasma concentrations for a single LBM.

FIG. 7 shows the actual infusion rate required for applying the curve of FIG. 6 curve (b) to patients of 20, 40, 60 and 80 kg LBM in order to achieve a steady plasma concentration of 1 mg/l of thiopentone. It can be seen that the shape of the generalized profile for plasma drug efflux remains the same as presented in FIG. 6 curve (b) but that the magnitude is altered throughout the profile in direct proportion to the Lean Body Mass of the patient.

Figure 8:
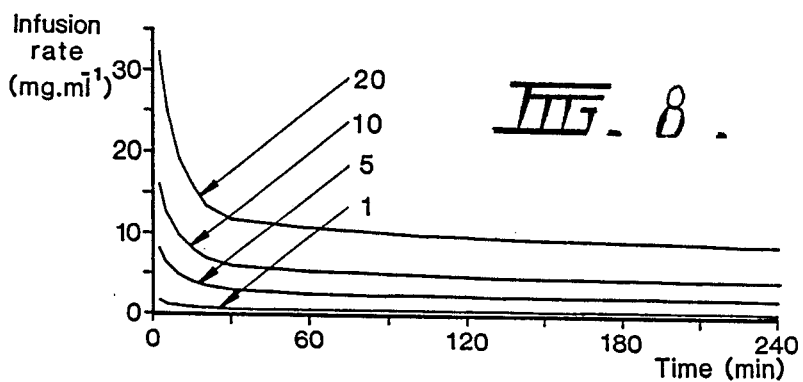

FIG. 8, demonstrates a further scaling operation of the curve of FIG. 6 curve (b) where the actual infusion rates required for a 50 kg LBM patient, in order to achieve steady plasma concentrations of 1, 5, 10 and 20 mg/l are presented.

It is of interest to note that in a further application of the technique of the invention to the anaesthetic agent methohexitone (methohexital) (FIG. 9) that the Plasma Drug Efflux profile, derived from actual infusion data for this drug after three iterations bears little relationship to an exponential function, having two distinct humps. It is of further interest to note that an application of the Efflux profile of FIG. 9 to generate an infusion in a typical patient (FIG. 10) has resulted in constant and desired arterial plasma drug concentrations over a period of five hours. The broken line in the Figure indicates the concentration desired by the operator. Similar results have been achieved on many patients with no material departures from the desired level in any patient.

It will be appreciated that the above method may be used to derive similar Plasma Drug Efflux profiles for other anaesthic agents and for other drugs where a desired level of the drug in the system of the patient is to be maintained over an extended period of time.

While the most commonly used intravenous anaesthetic agents, thiopentone and methohexitone, have been used as examples, the methods, and the apparatus to be described below, are equally applicable to the administration of all intravenous anaesthetic agents including propofol, diazepam, midazolam and etomidate, as well as narcotic analgesics including morphine, pethidine, alfentanil, sufentanil, fentanyl and phenoperidine.

It will be appreciated from the above that the Efflux profile may be used to control a programmable infusion pump so that a selected drug may be delivered to a patient in accordance with the profile, as scaled by the Lean Body Mass of the patient and level of the drug desired by the operator to be maintained in the system of the patient. The profile is most suitably programmed into a device capable of controlling the infusion pump and since a different profile is required for each drug, this is most suitably achieved by the use of a programmed module which is inserted by the operator into the infusion pump controller circuit. One preferred embodiment of such an infusion pump will now be described.

By using the average rate of loss of the drug among different subjects against time an infusion pattern is produced which approaches the optimal pattern. This new pattern may then be applied to the next group of patients so that an iterative process results whereby an optimized curve is produced.

Referring now to FIGS. 11 to 17, a preferred embodiment of the infusion pump for performing the drug infusion method and its control circuitry is shown. The infusion pump will be seen to comprise a casing 100 within which the syringe drive and other mechanisms described below are located, the casing 100 including a syringe cradle 101 having a central groove 102 for locating the body of a syringe and a slot 103 for receiving and locating the syringe flange. A vertically moveable syringe holder and sizer 104 is positioned over the groove 102 and a syringe actuator 105, which is driven by the syringe drive in a manner further described below, is positioned to engage the syringe plunger to deliver fluid from the syringe at the rate determined by the syringe drive under the influence of its control circuitry.

The casing is also provided with a front panel 106 including the required input keys and displays. The casing further includes a window 107 through which the name of the program drug appearing on a program module 108 which is inserted into a receiving cavity in the casing 100 in the direction of the arrow, may be read.

Figure 12:
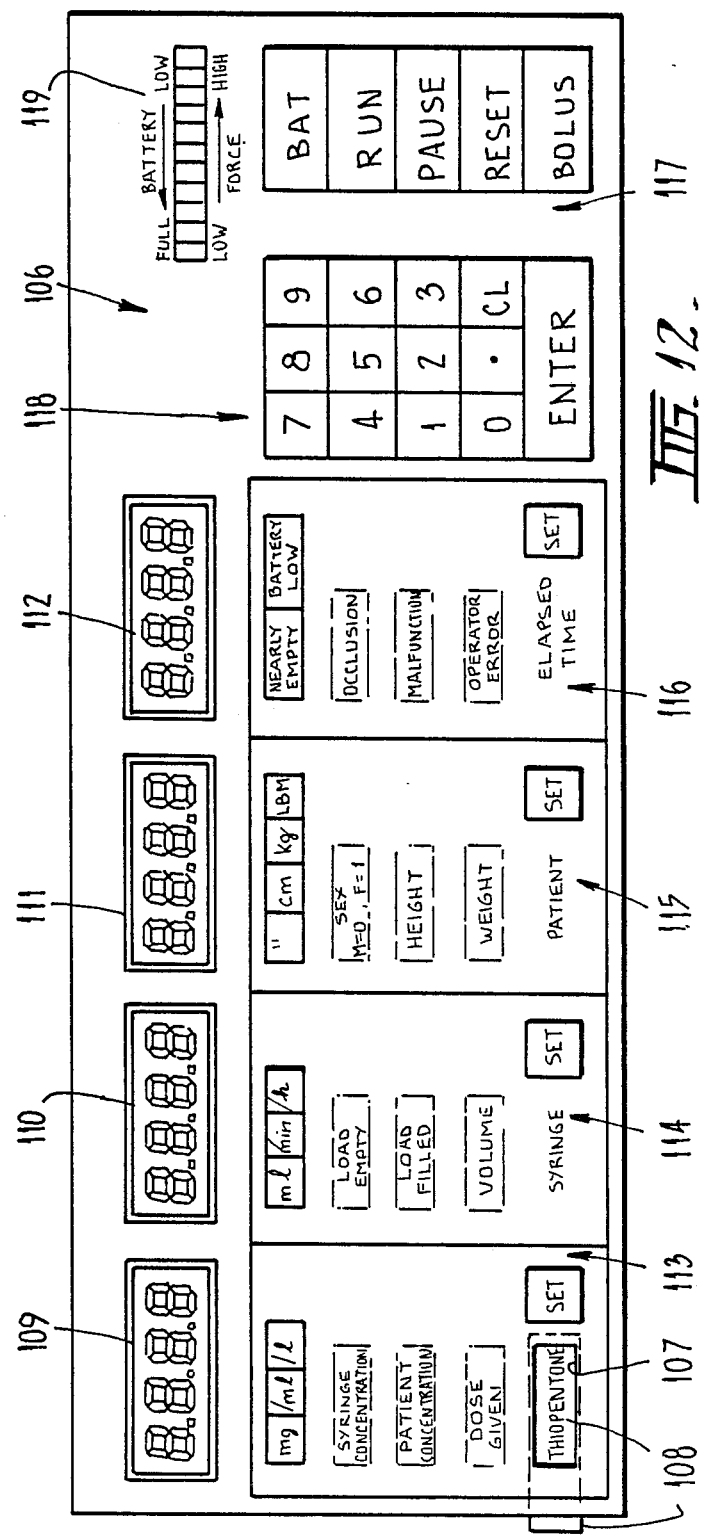
FIG. 12 is a plan view of the control panel of the pump of FIG. 11.

Referring now to FIG. 12, the front panel 106 will be seen to include 4 four digit LCD displays 109, 110, 111 and 112. The first display 109 is associated with a first sector 113 of the panel 106 and includes illuminatable message displays for syringe concentration, patient concentration and dose given as well as the alternative measurement displays mg. mg/ml or mg/l. Thus when the relevant displays are illuminated, the four digit display indicates the level of the illuminated parameter.

The second display 110 is associated with a second sector 114 of the panel 106 which relates to the syringe and the rate of infusion therefrom. The infusion rate may be displayed in ml/min or ml/h by actuating an option switch inside the casing 100. The volume in the syringe is displayed in ml.

The third display 111 is associated with a third sector 115 which displays patient data including illuminatable displays which prompt the selection of male or female and prompt the inputting of the patients height and weight. A further option select switch is available to indicate the height of the patient in inches rather than in centimeters.

The fourth display 112 is associated with a fourth sector 116 which relates to elapsed time and also includes illuminatable displays indicating the status of the battery, occlusion, malfunction and operator error.

To the right of sector 116 a fifth panel 117 includes a key pad 118 for numeric entry including a cancelled button and an enter button. The panel 117 also includes five selection buttons selecting the functions: battery power, run, pause, reset and bolus. A battery charge level indicator 119 is also provided in the front panel 106.

Numeric entry into any one of the displays 109 to 112 is achieved by scrolling through the data displays using the set button associated with the relevant panel sector 113 to 116 followed by entry of the value by means of the key pad 118. Once the desired value is displayed, the operator may press the enter button so that the value is entered into the memory of the control circuitry to be described below.

The infusion pump is capable of operating at three levels:

Level 1—The rate of infusion is entered directly on the front panel and the pump will deliver any solution at this rate only—or until the rate is manually changed.

Level 2—The rate can be set by a remote device such as a computer. The Infusion Pump will communicate with the remote device by means of an isolated serial port.

Level 3—The rate of delivery of certain anaesthetic drugs is determined by the EPROM module 108 which is plugged into the infusion pump casing 100. This module will vary the rate with time and the relationship between these two factors will depend on the type of drug. Consequently, a separate module will be required for each drug type.

The rate as read from the EPROM module 108 is normalised, and the control unit will scale this to the patients sex, weight and height, and to the desired concentration entered by the operator. These factors are entered on a front panel keyboard as described below. A serial port (Serial I/O option—FIG. 13) is an 'add-on' option capable of operating with or without an EPROM module plugged into the unit. Once appropriate control codes are sensed at the port, the unit will assume Level 2 operation. The serial port will also be capable of acting as a printer output for Level 1 or Level 3 operation.

Figure 13:
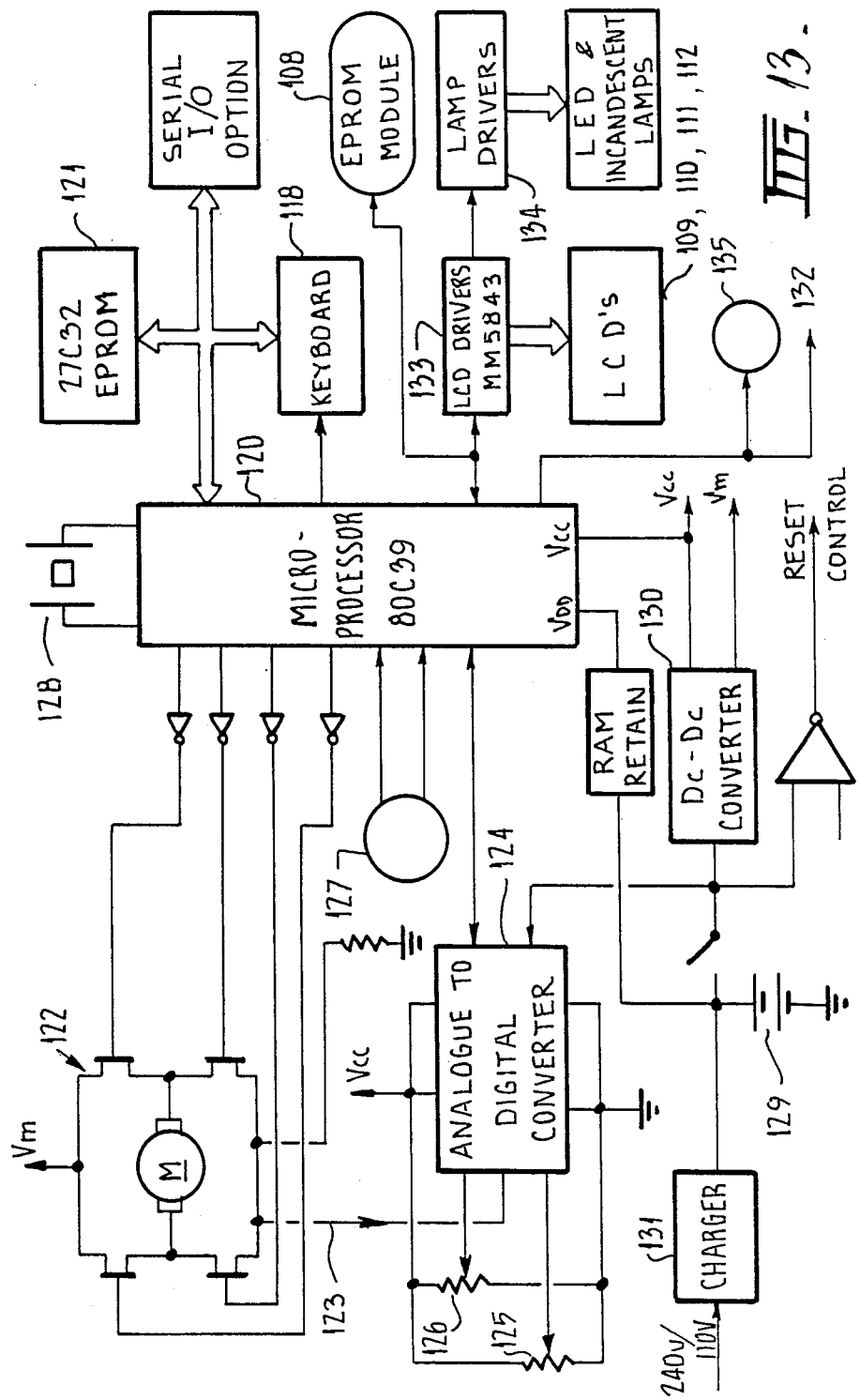
FIG. 13 is a block diagram of the control circuitry for the pump of FIG. 11.

Referring now to FIG. 13 of the drawings, the control circuitry for the infusion pump will now be described. Central to the control circuitry is a micro computer 120, which in the present embodiment is a type 80C39, which operates in accordance with an operating program stored in EPROM 121. The EPROM 121 my form part of the micro processor 120, and such a micro processor is available in the form of an 80C48. The micro processor 120 controls the speed of the motor in the syringe drive to be described below via a MOSFET driver circuit 122. The voltage applied to the motor via the circuit 122 is sensed by the line 123 which is connected to an analog to digital convertor 124 which also receives signals from feedback potentiometers 125 and 126 which respectively monitor the position of the syringe actuator 105 in FIG. 14, and indicate the syringe size via movement of the syringe sizing arm 104. Each feedback potentiometer 125, 126 is preferably a ten turn 50k ohm wire wound potentiometer since such potentiometers are accurate, reliable and inexpensive. An optical encoder 127, which forms part of the motor monitors the speed of the motor and feeds this data to the micro processor 120 so that the speed of the motor is accurately controlled by the micro processor 120.

A 6 MHz crystal clock signal generator 128 is connected to the micro processor 120 to enable the necessary timing functions to be performed. The micro processor 120 and the motor are powered by means of a battery 129 which is connected to the micro processor 120 and to the motor drive circuit 122 via a DC-DC convertor 130 which removes any unwanted variations in the battery supply voltage. A charger 131 is provided to enable the battery 129 to be recharged.

The micro processor 120 is also connected to a switch 132 positioned on the syringe actuator 105 with closure of the switch 132 indicating that the contact between the syringe actuator 105 and the syringe plunger has occurred. The switch 132 is preferably a single pole double toggle switch which indicates not only when contact between the syringe actuator 105 and the syringe plunger has occurred but also when disengagement between the syringe actuator 105 and the syringe plunger has occurred. Although this arrangement is presently preferred, it is also possible for the micro processor 120 to sense when the current drawn by the motor increases and decreases, via line 123, so that the engagement and disengagement between the syringe actuator 105 and the syringe plunger may be detected.

The LCD displays 109 to 112 are connected to LCD driver circuits 133 while the remaining indicator lamps and LED battery charge indicator 119 are connected to lamp driver circuits 134. A warning buzzer 135 is also provided for the purpose to be described further below.

The operating program stored in EPROM 121 causes the infusion pump to function in the following manner.

At "power on" all displays are illuminated for one second and then turned off. An internal test sequence is performed in which the presence of the drug specific EPROM module is detected and any malfunction in the displays is noted and, if so, the malfunction display illuminated. Thereafter, the initialisation sequence commences in which the "syringe concentration" display is illuminated and the units in mg/ml is displayed via the display 109 taking the usual concentration of the drug read from the module 108, for example, thiopentone—25 mg/ml, methohexitone—10 mg/ml, fentanyl—0.050 mg/ml. The operator may then press the set button in sector 113 or perform the numeric entry sequence for a desired syringe concentration value. The resulting syringe value, whether it remains as read from the EPROM or is altered by the operator, is stored in memory to be used to scale delivery of the drug containing fluid. After entry of this data or after the set button is pressed, the "patient concentration" display is illuminated and an average value as read from the module 108 is displayed at 109, for example, thiopentone 10.0 mg/l or methohexitone 5.0 mg/l. The displayed value may be modified by the numeric entry sequence described above. The EPROM module 108 stores an acceptable range of patient concentrations for each drug, for example, thiopentone 5–20 mg/l and methohexitone 2–12 mg/l. If values outside these ranges are entered then the 'patient concentration' display is flashed in all modes of operation until the value is brought within the range. On pressing the set button or the enter button, entry to this sector is complete and the first display on the syringe sector 114 ("load empty") is illuminated.

The operator raises the syringe holder and sizer 104 and loads an empty syringe into the syringe cradle 101 and presses the set button in sector 114. The motor is activated and the syringe drive to be described further below moves the syringe actuator 105 towards the empty syringe until closure of the switch 132 indicates contact and the position of the syringe actuator 105 is stored in the memory of the micro processor 120. This is the zero position (plunger length) of that particular syringe. The syringe diameter as detected by the syringe holder and sizer 104 through feedback potentiometer 126 is also stored in the memory. If no syringe is loaded, the previously stored zero position and syringe diameter are assumed and the syringe actuator 105 is driven fully to the left to await the loading of a filled syringe.

The "load filled" display is then illuminated and the operator loads a syringe and presses the set button. At this point, a comparison is made between the previous diameter and the new diameter and if a discrepancy of greater than ±2.5% is noted, the "load empty" display is illuminated in order to calibrate for a new syringe. If the new diameter matches the old then the "volume" display is illuminated and the volume of the syringe computed from the diameter of the syringe and the displacement of the syringe actuator 105 from the zero position is displayed at 110 and stored in the memory of the infusion device in order to adapt plunger movement to deliver the required volume as determined by other calculations. As an optional safety feature, the operator may be required to enter the loaded volume of the new syringe and if the entered value differs by more than ±10% of the previously computed value, the calibration procedure is recommenced from "load empty".

It has been found that the variation in wall thickness of commerically available syringes of similar internal diameters is insignificant when regard is had to the error tolerance in the volume of drug which may be infused into a patient as well as the acceptable error in the formulation of the drug solution. Accordingly, the diameter measurement which is made by the syringe holder and sizer 104 is sufficiently accurate to provide the necessary volume measurement during the infusion process.

After the filled syringe is loaded and the syringe actuator 105 is in contact with the syringe plunger, the "sex M=0 F=1" display is illuminated followed by the "height" and "weight" displays in sequence for numeric entry of the values relating to the particular patient to be treated. If the operator wishes to enter the patient height in inches, the internal switch is actuated. The operator enters these patient parameters, the Lean Body Mass is calculated, displayed on display 111 and stored in the memory of the device for use in adapting infusion rates to the particular patient. Once the patient data entry is completed, the set button is pressed and the display 112 will scroll through the values entered in sector 116, at which time any value may be changed by the numeric entry procedure.

After the patient data has been entered, all displays should be blanked except for the time which will show 00:00. At this stage, the elapsed time may be preset using the numeric entry sequence in the event that the pump needs to be restarted within an infusion sequence. The zero elapsed time or the operator preset time is indicated on display 112 and stored in the memory of the device for use in determining the point to start reading the infusion pattern.

When the patient is ready for treatment, the run button is pressed with the elapsed time incrementing, except during activation of the pause button, and shown on display 112. The syringe display 110 will show the delivery rate in ml/min or ml/h if the option switch has been actuated. The patient display 111 indicates the Lean Body Mass of the patient in kg calculated by the formula referred to above. The drug display 109 indicates the accumulated dose of drug administered to the patient.

Whenever the pause button is pressed, the time clock stops operation and the syringe display 110 indicates the total volume delivered since commencement of operation and the volume display is illuminated. The patient display remains unaltered while the drug display 109 indicates the dose given since the previous reset or commencement, the dose given display being illuminated at the same time.

It should be emphasized that by virtue of the syringe sizing mechanism and the plunger sensing switch of the device the accumulated volume and doses displayed will represent the sum of all syringes loaded whatever the volume or size of syringe used. Change of any display can occur at this point by pressing the appropriate set button and if the syringe holder and sizer 104 is lifted or the syringe actuator 105 is moved, the syringe sequence recommences at the "load filled" point.

If the bolus button is pressed at any time, the syringe and drug displays are immediately zeroed and drug delivery commences at a rate of the order of 1 ml/sec for a 50 ml syringe, the display "dose given" is illuminated and the progressive volume delivered is displayed at 110 in ml. On release of the bolus button, the syringe display reverts to a display of the running rate, the drug display 109 shows the sum of the bolus and the previous dose while the time display reverts to the previous mode.

Pressing the BAT button causes illumination of the LED display 119 to indicate the condition of the battery.

If either the syringe switch 132 or the syringe holder and sizer 104 is moved to a new position for more than two seconds, the syringe actuator 105 is driven to the left and the syringe set sequence is recommenced at the "load filled" point. If an occlusion is detected by a sudden increase in the drive current to the motor, via line 123, the syringe actuator 105 is driven to the left until the switch 132 is disengaged, whereupon the "occlusion" display is illuminated and the buzzer 135 actuated. The detection of occlusion is related to a diameter of the syringe, detected by the syringe sizing mechanism so that the larger drive current required for larger syringes will not cause a false occlusion alarm. One way of achieving this is to store data relating to the maximum force required to move a syringe at various rates in use and to scale this force in accordance with the detected diameter.

Occlusion of the drug delivering conduit by a tap represents considerable danger to a patient if a highly potent drug is contained in the syringe and the tap is suddenly opened while under pressure. The three features of adjusting occlusion pressure detection to the measured syringe diameter, backing of the drive once overpressure is detected and sounding the alarm after the pressure is removed are specifically designed to lessen this risk.

Illumination of the "malfunction" display occurs whenever any form of malfunction is identified and the buzzer 135 is actuated. Similarly, the "operator error" display will be illuminated in the event of an operator error being detected, such as, pushing forward manually on the drive mechanism when the drive mechanism is connected or the entry of incompatible syringe sizes for a given LBM. Syringe to patient incompatibility is determined by calculating the ratio of the Lean Body Mass of the patient to the sensed diameter of the syringe and relating this ratio to the rate fluid is to be delivered. It is recognized that considerable inaccuracy will result if a very large syringe is used with a very small patient.

As mentioned above, three levels of operation may be selected and the level of operation determines the rate at which the fluid in the syringe is delivered and this rate continues, as programmed, unless any one of the following occur:

the bolus key is depressed.
an occlusion occurs.
a system malfunction occurs.
the plunger is manually pushed forward to administer more fluid (as sensed by the plunger position potentiometer 125). The switch 132 shows the plunger is disengaged.
the syringe size potentiometer 126 indicates a change in reading, or
the pause key is pressed.

Figure 9:
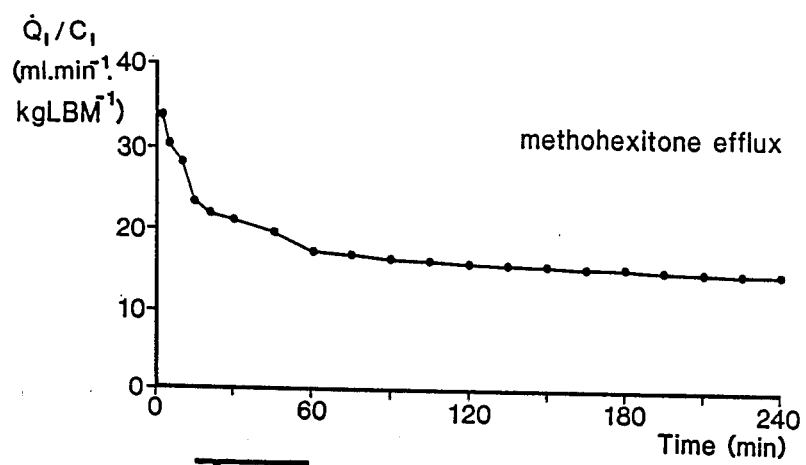
FIG. 9 is the Plasma Efflux profile for methohexitone (methohexital) after three iterations.

In Level 3 operation, an infusion pattern stored in the EPROM 108 is followed by the infusion pump. The pattern is drug dependent and a separate module 108 is used for each type of drug. Typical infusion patterns for thiopentone and methohexitone are shown in FIGS. 6 and 9 of the drawings and are described in greater detail above. The rate drug delivery stored in the module 108 is scaled by the Lean Body Mass data entered in the manner described above as well as by the desired concentration data entered by the operator. The effect of this scaling is clearly shown in FIGS. 7 and 8 of the drawings which indicate drug delivery rate in terms of the dose delivered per minute. The volume of drug containing fluid which must be delivered is further scaled in accordance with usual concentration of the particular drug in the syringe which is read from the drug specific EPROM 108 or entered by the operator during the initialization sequence. Then using the result of these previous calculations the actual movement of the syringe actuator is scaled in proportion to the syringe diameter as determined by the syringe sizing mechanism.

During Level 3 operation, a bolus is automatically administered at time 00:00 unless the operator indicates, via keyboard input, that a bolus has been previously administered.

This starting bolus is administered at a rate determined by data stored in the EPROM module 108, the volume administered being scaled according to the entered Lean Body Mass desired concentration and the concentration of drug in the syringe. The amount delivered is displayed at 109 with the "dose given" display illuminated.

During normal operation additional drug may be administered by pressing the bolus key and will continue at the rate described above for as long as the key is depressed.

Referring now to FIGS. 14 to 17 of the drawings, the syringe drive mechanism will now be described in greater detail.

Figure 14:
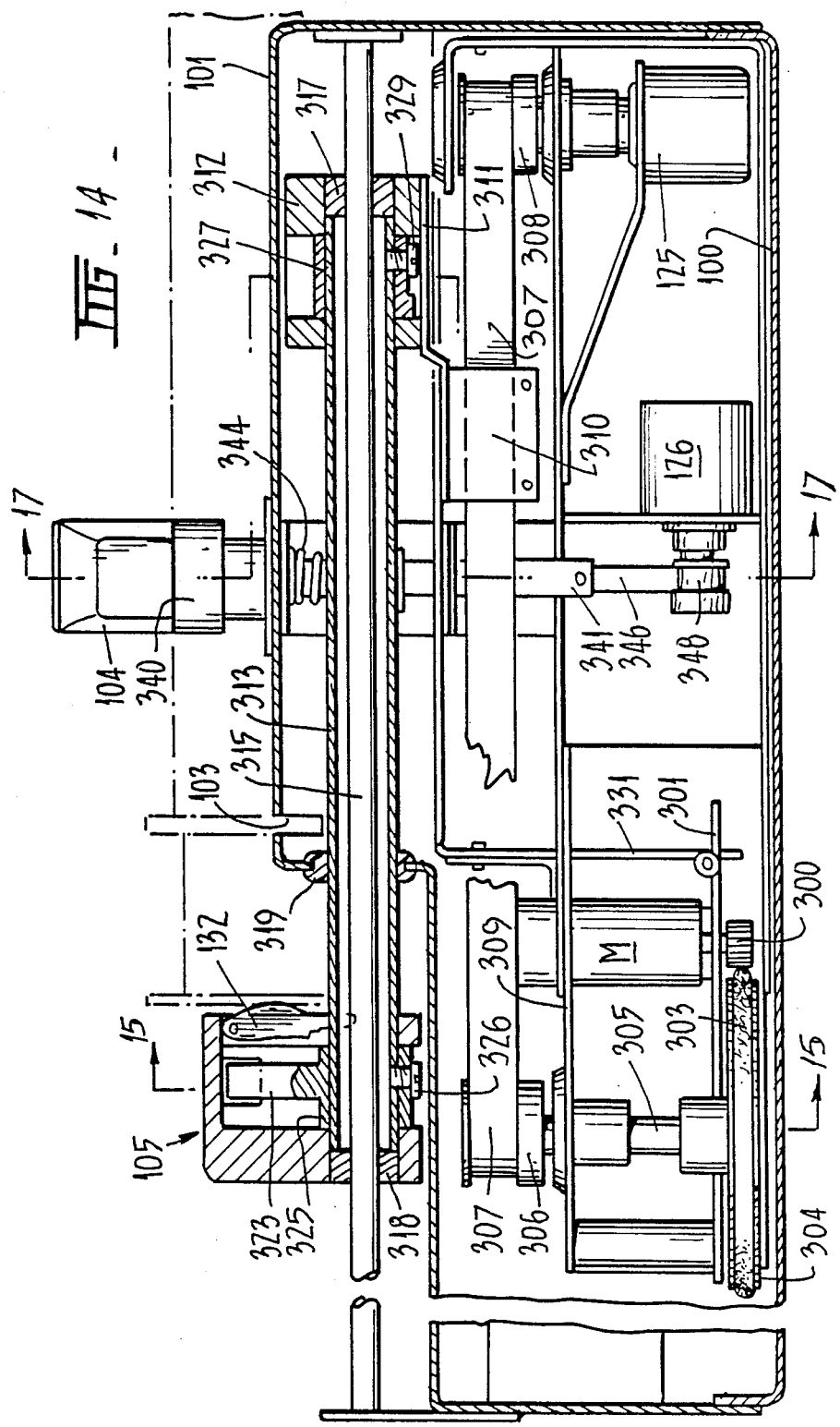
FIG. 14 is a section front elevation of the pump of FIG. 11 taken along the line 14—14 in FIG. 11.
Figure 15:
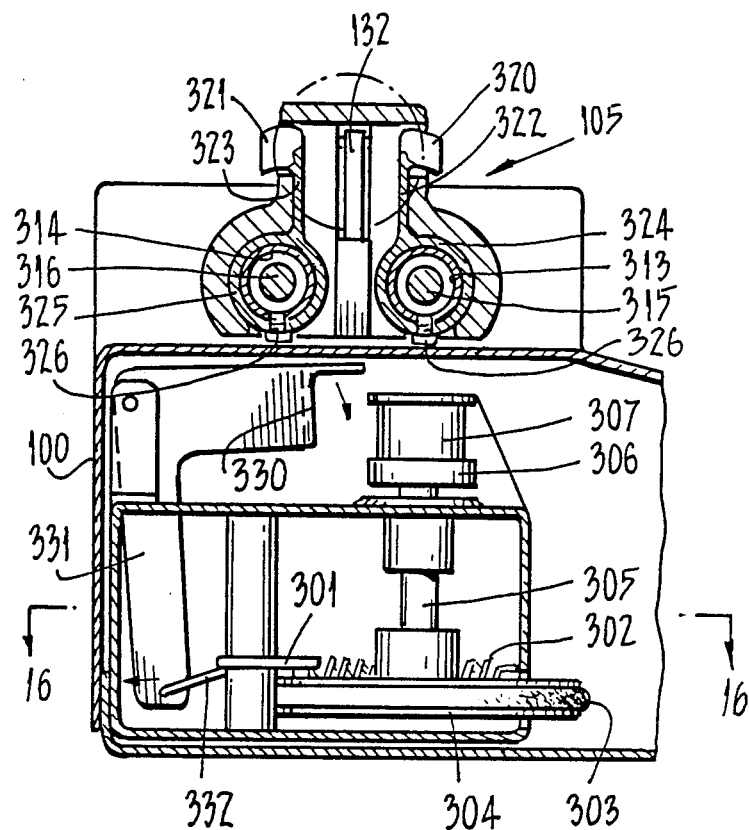
FIG. 15 is a sectional elevation taken along the line 15—15 in FIG. 14.
Figure 16:
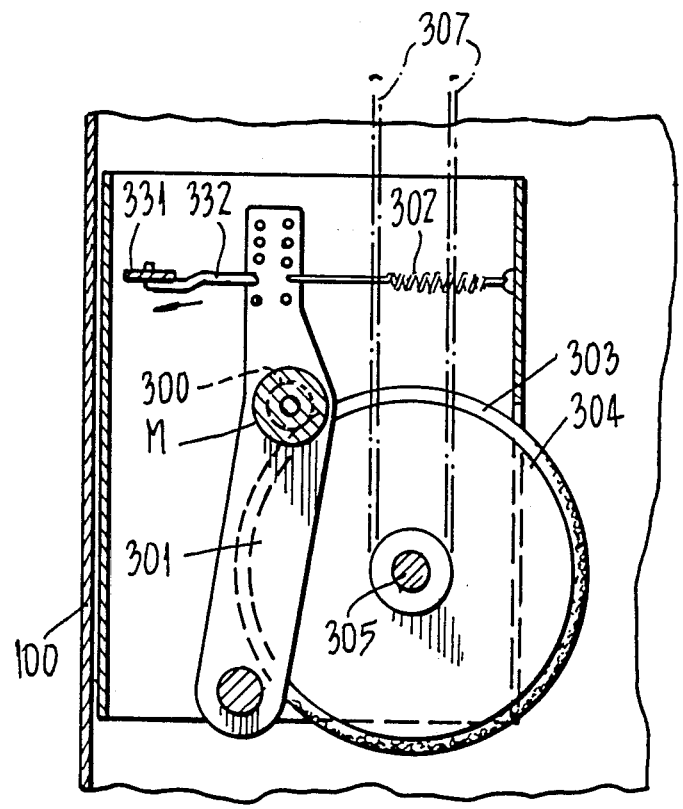
FIG. 16 is a sectional plan view taken along the line 16—16 in FIG. 15.

The drive motor M is preferably an ESCAP DC gear motor type MA1616 C11 with 243:1 gear ratio and B type optical encoder. The output shaft of motor M is fitted with a toothed or knurled drive wheel 300 and the motor is mounted on a pivoted arm 301 (FIG. 16) which is pivoted towards its "drive engaged" position under the influence of a spring 302. The drive wheel 300 engages a polyurethane drive ring 303 which encircles a driven wheel 304 which transmits drive through a shaft 305 to a toothed drive head 306. A toothed drive belt 307 engages the drive head 306 and also passes around a similar toothed drive head 308 spaced from the drive head 306 at the opposite end of the casing 100. Both drive heads 306, 308 are mounted in bearings on a frame 309 and the drive head 308 is drivingly connected to the position feedback potentiometer 125 which is supported below the frame 309 in the manner shown (FIG. 14). It should be appreciated that the belt drive may be replaced by a chain or similar flexible drive although the belt drive is preferred for practical reasons.

A permanent driving connection is effected between the drive belt 307 and the syringe actuator 105 by means of belt clamp 310 having a connector plate 311 which is in turn attached to a slider 312 which is connected to the syringe actuator 105 by means of tubes 313, 314 surrounding a pair of spaced parallel guide rods 315, 316 which extend longitudinally of the casing 100 and into the syringe cradle 101. Both the slider 312 and the syringe actuator 105 are provided with bearings 317, 318 which engage the guide rods 315, 316 to facilitate sliding movement of the slider 312 and the syringe actuator 105. The tubes 313, 314 engage seals 319 in the syringe cradle 101 to prevent ingress of foreign matter into the casing 100.

It will be appreciated from the above that a permanent driving connection is maintained between the belt 307 and the syringe actuator 105 so that the position potentiometer 125 is at all times able to accurately sense the position of the syringe actuator 105. In other words, there is not in the present embodiment of the invention, as in some prior art infusion pumps, the ability to disconnect the drive between the syringe actuator and the driving mechanism. However, it is possible to disengage the drive wheel 300 from the driven wheel 304 to enable easy manual movement of the syringe actuator 105 during loading and unloading of a syringe.

In the present embodiment, drive release is achieved by manually depressing push buttons 320, 321 mounted in the syringe actuator 105. The buttons 320, 321 extend from the ends of arms 322, 323 which in turn extend from mounting sleeves 324, 325 which surround the tubes 313, 314 and are fixed to impart rotation thereto by means of grub screws 326 when the buttons 320, 321 are depressed. It will be appreciated from the above that the tubes 313, 314 are free to rotate in both the syringe actuator 105 and the slider 312.

Drive release actuating cams 327, 328 are attached to tubes 313, 314 by means of grub screws 329 and are located within the slider 312. The cams 327, 328 are positioned to contact a motor release bar 330 (FIGS. 15 and 17 which is in the form of a bell-crank lever having its pivot extending longitudinally of the casing 100. The other arm 331 of the bell-crank lever is attached by a link 332 (FIGS. 15 and 16) to the pivoted motor mounting plate 301. Thus by depressing the buttons 320, 321, with one hand, the tubes 313, 314 are rotated to bring the cams 327, 328 into contact with the motor release bar 330 which pivots the plate 301 to the left in FIG. 16 to move the drive wheel 300 out of engagment with the rim 303 of the driven wheel 304. When thus released, the syringe actuator 105 may be freely moved along the guide rods 315, 316 although by virtue of the permanent connection to the drive belt 307, the position sensing potentiometer 125 continues to register the position of the syringe actuator 105 at all times.

It will be appreciated that motor release may be achieved with only one button and associated tube and cam mechanism.

Figure 17:
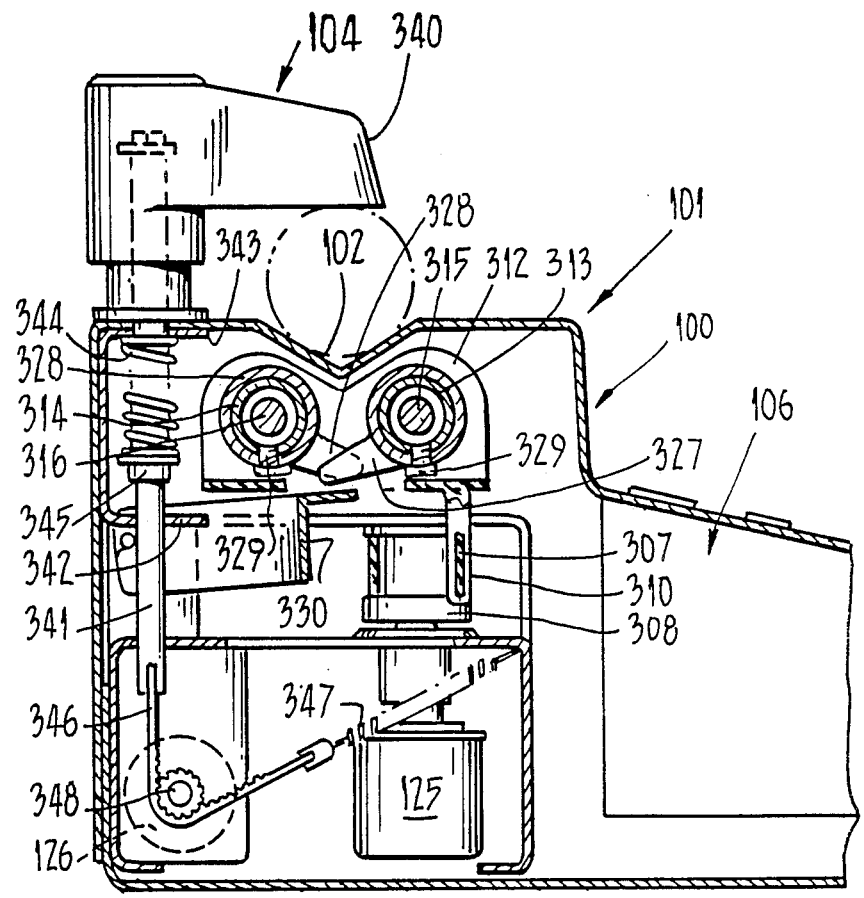
FIG. 17 is a sectional end elevation taken along the line 17—17 in FIG. 14.

Referring now to FIGS. 14 and 17, the syringe holder and sizer 104 will be seen to comprise a clamping arm 340 mounted on a vertically extending shaft 341 supported for vertical sliding movement by frame members 342, 343 and biased towards a clamping position by means of compression spring 344 engaging a flange retainer 345 attached to the shaft 341. At its lowermost end, the shaft 341 has an element of toothed drive belt 346 attached thereto and a light biasing spring 347 is attached to the other end of the belt 346 to maintain it in engagement with a gear wheel 348 keyed to th shaft of the syringe sizing potentiometer 126. In this way the syringe holder and sizer 104 operates to clamp the syringe in the syringe cradle 101 and causes the sizing potentiometer 126 to transmit a syringe size signal to the micro processor 120 via the analog to digital convertor 124.

The rating of the spring 302 is selected so that the driving gear 300 will slip on the rim 303 of the driven wheel 304 in the event that a severe occlusion occurs and the syringe plunger does not move into the syringe. Of course in most instances, the micro processor 120 will sense an excessive increase in motor current and will stop the motor M.

What we claim is:

1. A method of infusion of a drug into a patient comprising the steps of:
   (i) determining the Lean Body Mass of the patient;
   (ii) selecting a predetermined profile for the rate of delivery of drug, which rate reduces with time and is configured to maintain a selected substantially steady plasma arterial content of the drug in the patient throughout an infusion period; said profile being determined by:
   (a) infusing a drug at arbitrary but known rates into a group of patients for each of whom the Lean Body Mass has been determined;
   (b) determining the plasma arterial concentration of the drug in each patient at a number of specific time intervals throughout each infusion period;
   (c) for each patient, estimating the rates of loss of drug from the circulation at a number of specific time instants by dividing the known infusion rates per Lean Body Mass of these instants by the plasma arterial concentrations of the drug at each of these instants;
   (d) calculating the average of the estimated rates of loss of drug from the circulation per Lean Body Mass unit at each specific time interval for the group of patients;
   (e) interpolating the successive average points between the specific time intervals to produce an infusion profile;
   (f) infusing said drug in accordance with said infusion profile determined from said interpolations into a group of patients for each of whom the Lean Body Mass has been determined, said infusion rate being scaled according to said Lean Body Mass of each patient, and
   (g) repeating steps (b) to (f) until a desired steady plasma arterial content of the drug is substantially maintained throughout the infusion period;
   (iii) scaling said predetermined infusion profile by the determined Lean Body Mass of the patient and by the desired substantially steady plasma arterial content of the drug to be maintained in the system of the patient, and
   (iv) administering the drug to the patient in accordance with said scaled profile by means of an infusion device which is controlled to deliver said drug at said scaled infusion rate profile.

2. The method of claim 1, wherein said predetermined drug delivery rate profile is stored in a storage device which controls said infusion device at a rate which is subjected to said scaling.

3. The method of claim 2, wherein said storage device is a programmable read only memory which co-operates with a micro processor to control said infusion device.

4. An infusion system for regulating the delivery of a drug to a patient, including control means for controlling the operation of an infusion pump, said control means including pre-programmed means for varying the infusion rate with respect to elapsed time, said pre-programmed means varying the infusion rate in accordance with a profile which varies with time and which is adapted to maintain a desired substantially steady plasma arterial content of the drug throughout the infusion period; said profile being determined by:
   (a) infusing a drug at arbitrary but known rates into a group of patients for each of whom the Lean Body Mass has been determined;
   (b) determining the plasma arterial concentration of the drug in each patient at a number of specific time intervals throughout each infusion period;
   (c) for each patient, estimating the rates of loss of drug from the circulation at a number of specific time instants by dividing the known infusion rates per Lean Body Mass of these instants by the plasma arterial concentrations of the drug at each of these instants;
   (d) calculating the average of the estimated rates of loss of drug from the circulation per Lean Body Mass unit at each specific time interval for the group of patients;
   (e) interpolating the sucessive average points between the specific time intervals to produce an infusion profile;
   (f) infusing said drug in accordance with said infusion profile determined from said interpolations into a group of patients for each of whom the Lean Body Mass has been determined, said infusion rate being scaled according to said Lean Body Mass of each patient, and
   (g) repeating steps (b) to (f) until a desired steady plasma arterial content of the drug is substantially maintained throughout the infusion period; and operator adjustable scaling means for setting the desired concentration of said drug in the patient, for setting the Lean Body Mass of the patient, said scaling means causing modification of the pre-programmed infusion rate by a fixed proportion over each time period of operation of said infusion pump.

5. The system of claim 4, wherein said pre-programmed means comprises a read only memory module containing said profile relating to the drug to be administered, said control means including a port for receiving said module.

6. The system of claim 4 or claim 5, including operator adjustable scaling means for setting the concentration of said drug in a fluid containing said drug.

7. The system of claim 5, wherein said read only memory module contains information related to the drug to be delivered, including the usually prescribed concentration of the drug in a fluid containing such drug, an average plasma concentration for achieving an effect in the patient with the drug and an acceptable range of plasma concentrations of the drug.

8. The system of claim 4, wherein said infusion pump comprises means for receiving a syringe containing a drug-containing fluid to be administered, syringe actuator means and means for driving said actuator means to move the plunger of said syringe to deliver fluid therefrom, said drive means including a permanently maintained connection between said drive means and a position sensing device by means of which the position of said actuator means is monitored at all times.

9. The system of claim 8, wherein said drive means comprises a motor and a drive train driven by said motor, said drive train including said permanently maintained connection, and means for disconnecting drive between said motor and said drive train to enable said actuator means to be freely moved whilst maintaining said permanent connection so that the position of said actuator means is monitored.

10. The system of claim 9, wherein said drive train includes a driven wheel, a driving head connected to be driven by said driven wheel, a further driving head spaced from said driving head and a flexible driving connection interconnecting said driving heads so that said further driving head is positively driven by said driving head.

11. The system of claim 10, wherein said flexible driving connection comprises a toothed belt, the teeth of which positively engage teeth formed on said driving heads.

12. The system of claim 11, wherein said permanently maintained connection comprises a plate clamped to said belt and rigidly secured to means for moving said actuator means.

13. The system of claim 12, wherein said position sensing device comprises a rotary potentiometer driven by said further drive head, the output of said potentiometer being connected to control circuitry for said motor whereby the position of said actuator means is sensed.

14. The system of claim 9, wherein said means for disconnecting drive between said motor and said drive train comprises manually actuatable means on said actuator means.

15. The system of claim 14, wherein said means on said actuator means comprises at least one depressible lever which causes actuation of a further lever which disengages said motor from said drive train.

16. The system of claim 15, wherein said motor is mounted on a pivoted arm to which a bell-crank lever is connected by a linkage a said bell-crank lever being actuated by depression of said at least one lever.

17. The system of claim 16, wherein said actuator means supports two manually operable levers which are in turn connected to tubes rotatably mounted in the actuator means and slideably supported by guide rails, said tubes also being rotatably mounted in a slider spaced from said actuator means and to which said permanently maintained connection is attached, said tubes supporting cams which engage a motor releasing lever when said levers carried by said actuator means are manually depressed to disengage said motor from said drive train.

18. The infusion system of claim 8, further comprising a syringe holding and sizing means in the form of a syringe clamp to which a sizing mechanism is connected.

19. The system of claim 18, wherein said sizing mechanism comprises a rotary potentiometer, the output of which is connected to control circuitry for said pump whereby the diameter of the syringe is automatically measured thereby enabling the calculation of the volume of said syringe.

20. The system of claim 8, further comprising control circuitry for said pump which controls the rate of delivery of said drug containing fluid, said control circuitry including a programmable module which is pre-programmed with information concerning each drug to be administered by means of said infusion pump according to a predetermined profile which varies with time and which maintains a desired substantially steady level of the drug in the patient to whom the drug containing fluid is delivered.

21. The system of claim 20, wherein said control circuitry further comprises means for scaling the programmed profile in said module in accordance with the estimated Lean Body Mass of the person, the desired level of drug to be maintained in the person.

22. The system of claim 8, further comprising a switch mounted on said actuator means and positioned to engage the plunger of a syringe supported by said pump, said switch being connected in control circuitry for said pump to indicate that the actuator means has engaged a syringe mounted on said pump.

23. The system of claim 20, wherein means is provided for varying the rate of delivery of said drug containing fluid in accordance with a variation in the concentration of the drug in the fluid.

24. The system of claim 23, wherein means is provided for entering a variation in the concentration of the drug in the fluid.

25. The system of claim 8, .comprising means for displaying the quantity of drug infused.

26. The system of claim 8, including means to detect a pressure greater than a predetermined pressure required to deliver fluid.

27. The system of claim 19 or 26, including means to vary said predetermined pressure in relation to variation in syringe size.

28. The system of claim 22 or 24, including means to determine that an overpressure has been released.

29. The system of claim 8, 19 or 22, including means for detecting a syringe replacement, a variation in syringe size and means adapted to store an accumulation of drug dosage consequent on syringe replacement and/or variation of syringe size.

* * * * *